United States Patent
Zhang et al.

(10) Patent No.: US 12,122,756 B2
(45) Date of Patent: Oct. 22, 2024

(54) BIFLAVONE COMPOUND AGAINST I-TYPE HERPES SIMPLEX VIRUS, AND PREPARATION METHOD THEREFOR AND USE THEREOF

(71) Applicants: SICHUAN ACADEMY OF SCIENCES OF TRADITIONAL CHINESE MEDICINE, Sichuan (CN); Lei Zhang, Sichuan (CN); Chongjun Yuan, Sichuan (CN)

(72) Inventors: Lei Zhang, Sichuan (CN); Chongjun Yuan, Sichuan (CN); Mingming Yuan, Sichuan (CN); Shuai Chen, Sichuan (CN); Wei Yang, Sichuan (CN); Sen Luo, Sichuan (CN); Xia Wu, Sichuan (CN)

(73) Assignees: SICHUAN ACADEMY OF SCIENCES OF TRADITIONAL CHINESE MEDICINE, Sichuan (CN); Lei Zhang, Sichuan (CN); Chongjun Yuan, Sichuan (CN)

( * ) Notice: Subject to any disclaimer, the term of this patent is extended or adjusted under 35 U.S.C. 154(b) by 0 days.

(21) Appl. No.: 18/687,803

(22) PCT Filed: Aug. 22, 2022

(86) PCT No.: PCT/CN2022/113956
§ 371 (c)(1),
(2) Date: Feb. 28, 2024

(87) PCT Pub. No.: WO2023/138049
PCT Pub. Date: Jul. 27, 2023

(65) Prior Publication Data
US 2024/0287014 A1    Aug. 29, 2024

(30) Foreign Application Priority Data
Jan. 19, 2022    (CN) .......................... 202210058917.1

(51) Int. Cl.
*A61P 31/22*    (2006.01)
*A61K 31/352*    (2006.01)
*C07D 311/36*    (2006.01)

(52) U.S. Cl.
CPC .......... *C07D 311/36* (2013.01); *A61K 31/352* (2013.01); *A61P 31/22* (2018.01)

(58) Field of Classification Search
CPC ...... C07D 311/36; A61P 31/22; A61K 31/352
See application file for complete search history.

(56) References Cited

FOREIGN PATENT DOCUMENTS

| CN | 1594308 A | 3/2005 |
|---|---|---|
| CN | 101585825 A | 11/2009 |
| CN | 101723926 A | 6/2010 |
| CN | 101744805 A | 6/2010 |
| CN | 102091086 A | 6/2011 |
| CN | 106554339 A | 4/2017 |
| CN | 111018821 A | 4/2020 |
| CN | 113546075 A | 10/2021 |

(Continued)

OTHER PUBLICATIONS

Han et al., "In vitro evaluation of tectoridin, tectorigenin and tectorigenin sodium sulfonate on antioxidant properties," Food and Chemical Toxicology (2012), 50(2), 409-414 CODEN: FCTOD7; ISSN: 0278-6915. (Year: 2012).*

(Continued)

*Primary Examiner* — Jared Barsky
(74) *Attorney, Agent, or Firm* — NKL Law; Allen Xue

(57) ABSTRACT

A biflavone compound against an I-type herpes simplex virus, and a preparation method therefor and the use thereof. The bioflavone compound is a compound of formula I, or a crystal form thereof, or a salt thereof, or a stereoisomer thereof, or a solvate thereof, or a hydrate thereof, or a prodrug thereof. The biflavone compound has a good inhibitory effect on the I-type herpes simplex virus, has a significant effect on the replication and direct inactivation of the virus, and is dose dependent. The compound is also effective in preventing and/or treating viral keratitis caused by the I-type herpes simplex virus. The compound has good water solubility and low toxicity. It can be prepared into an external preparation for resisting the I-type herpes simplex virus, such as eye drops and eye ointment, and external ointments, creams, gel agents, film agents, film-coating agents, etc.

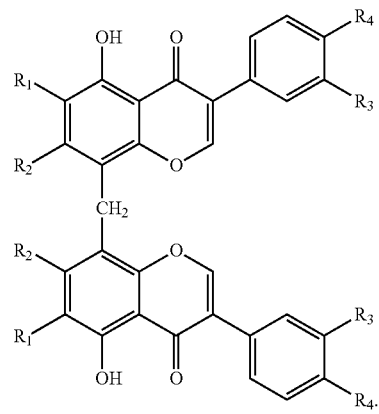

Formula I

11 Claims, 17 Drawing Sheets

(56) References Cited

FOREIGN PATENT DOCUMENTS

CN         114394950 A      4/2022

OTHER PUBLICATIONS

Yuan, Chongjun et al.; "Research on the Development of Sichuan Genuine Medicinal Material Chuanshegan System(Summary)"; Journal of Sichuan of Tranditional Chinese Medicine; vol. 34, Issue. 10; Year: 2016; pp. 220-223.

Tang, Sharon et al.; "Biflavonoids with cytotoxic and antibacterial activity from Ochna macrocalyx"; Planta Medica; Dec. 31, 2003; pp. 247-253.

* cited by examiner

FIG. 16

BIFLAVONE COMPOUND AGAINST I-TYPE HERPES SIMPLEX VIRUS, AND PREPARATION METHOD THEREFOR AND USE THEREOF

TECHNICAL FIELD

The present invention belongs to the technical field of chemical drugs, and specifically relates to a biflavone compound against herpes simplex virus type I (HSV-I), a preparation method therefor, and uses thereof.

BACKGROUND TECHNOLOGY

Rhizoma Iridis Tectori (named "Chuang She Gan" in Chinese) is the dry rhizome of *Iris tectorum* Maxim, a plant of family Iridaceae, which has the effects of clearing heat, detoxifying, eliminating phlegm, and throat-clearing, and thus is used for the treatment of toxic heat, stagnation of phlegm-fire, sore throat, phlegm-fluid accumulation, as well as cough and dyspnea. Modern pharmacology has confirmed that Rhizoma Iridis Tectori has extensive antiviral activity, especially in killing viruses that cause upper respiratory tract infections, such as adenovirus, rhinovirus, influenza virus, respiratory syncytial virus, and Coxsackie virus. Tectoridin and tectorigenin are its antiviral active ingredients, and based on the flavonoid compounds synthesized from tectorigenin as the mother compound, that exhibit antiviral activities against upper respiratory tract infection virus, some invention patents have been granted, such as CN1594308A, CN101723926B, and CN106554339B. However, due to the structural characteristics of flavonoids themselves, it is hard for them to be absorbed by gastrointestinal tract, and their water-soluble injections have problems of fast metabolism and short half-life, which limit their clinical application (Yuan Chongjun, Chen Shuai, Luo Sen, et al. Chuanshegan System Development Research from Genuine Medicinal Materials in Sichuan [J]. Journal of Sichuan of Traditional Chinese Medicine, 2016, 34(10): 220-223).

Herpes simplex virus type I (HSV-I) mainly causes infections of the skin, mucosa (oral mucosa), and organs (brain) outside the genitalia, such as herpes simplex keratitis, conjunctivitis, and labial herpes. There is currently no vaccine available, and symptomatic treatment or antiviral drugs such as ribavirin, acyclovir, and penciclovir are often used internally or externally in clinical practice. However, the long-term use of antiviral drugs can lead to resistance, especially in patients with low immune function. Therefore, it is necessary to search for other drugs against HSV-I infection and replication, with different mechanisms of action.

Biflavonoid compounds have greater molecular flexibility than flavonoids, can bind to many different receptors, and theoretically have many pharmacological activities. For example, patent 202111051370.4 discloses a biflavonoid compound with anti-tumor effects. However, due to the unpredictability of the efficacy of chemical drugs, how to find biflavone compounds with pharmacological activities is a research challenge. If a biflavone compound against HSV-1 can be found, it will be of great significance for inhibiting HSV-1 in the clinic.

SUMMARY OF THE INVENTION

The present invention aims to provide a biflavone compound against HSV-I, as well as its preparation method and uses.

The present invention provides a compound represented by formula I, or a crystal form thereof, or a salt thereof, or a stereoisomer thereof, or a solvate thereof, or a hydrate thereof, or a prodrug thereof:

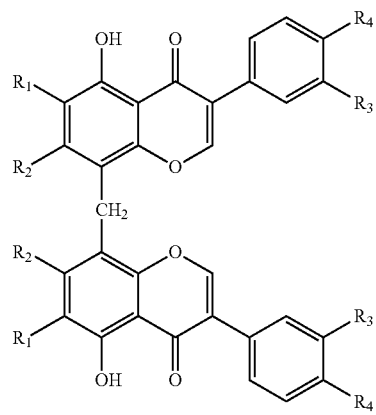

Formula I wherein, $R_1$, $R_2$, $R_3$, and $R_4$ are each independently selected from the group consisting of $C_1$-$C_8$ alkyl, $C_1$-$C_8$ alkoxy, hydroxyl, halogen, amino, nitro, carboxyl, and —$SO_3R_5$;

$R_5$ is selected from the group consisting of Na and K.

Further, $R_1$, $R_2$, $R_3$, and $R_4$ are each independently selected from the group consisting of $C_1$-$C_3$ alkyl, methoxy, ethoxy, hydroxyl, and —$SO_3R_5$;

$R_5$ is selected from the group consisting of Na and K.

Further, the compound is represented by formula II:

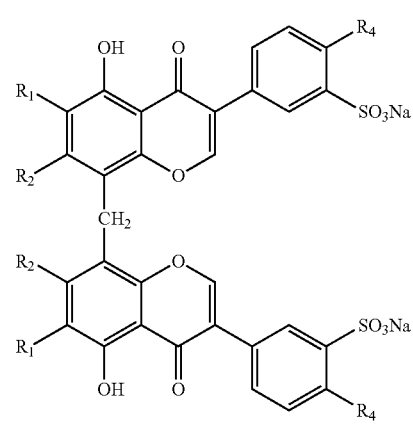

Formula II wherein, $R_1$, $R_2$, and $R_4$ are each independently selected from the group consisting of $C_1$-$C_3$ alkyl, methoxy, ethoxy, and hydroxyl.

Further, the compound is that having the following structure:

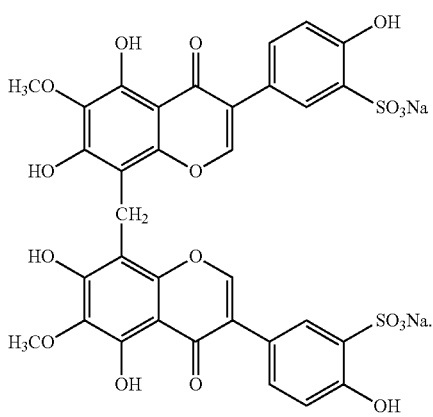

The present invention also provides a method for preparation of the above compound, which comprises the following steps:

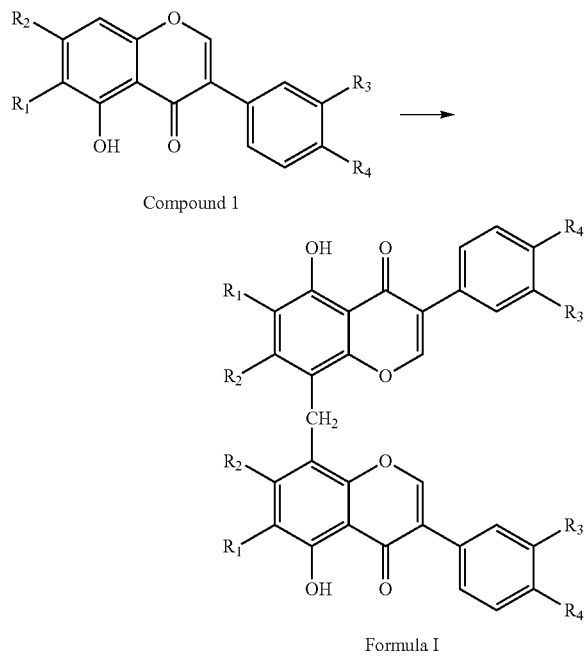

Compound 1

Formula I (1) Compound 1 is allowed to react with formaldehyde in a solvent to obtain the crude compound of formula I;
(2) The crude compound of formula I is purified to obtain the pure compound;
wherein, $R_1$, $R_2$, $R_3$, and $R_4$ are as defined in the above.
Further,
in step (1), the solvent is water or formaldehyde;
and/or, in step (1), the weight/volume ratio of compound 1 to formaldehyde is 1:(5-10) g/ml;
and/or, in step (1), the reaction is carried out by heating under reflux in a water bath for 8-10 hours;
and/or, in step (1), the solvent is recovered under reduced pressure, followed by drying, to obtain the crude product.
Further,
in step (2), the purification is performed by preparative HPLC, silica gel column chromatography, thin-layer chromatography, silica gel dry column chromatography or Sephadex gel column chromatography;
preferably, The conditions for purification using a preparative HPLC are as follows: the packing material for preparation column is octadecylsilane chemically bonded silica gel; the column temperature is room temperature; the mobile phase is a mixed solvent of methanol and water with a volume ratio of 30:70, with a flow rate of 10 ml/min;
and/or, the conditions for purification by silica gel column chromatography are as follows: the sample is wet loaded in pre-packed silica gel column in chloroform, and gradiently eluted using a mixed solution of chloroform and methanol with a volume ratio of 10:1, 5:1, 2:1, and 1:1; the volume/weight ratio of eluent to crude compound of formula I for each gradient is 500 ml:1 g;
and/or, the conditions for purification by thin layer chromatography and silica gel dry column chromatography are as follows: a mixed solution of chloroform and methanol with a volume ratio of 100:30 is used as the eluent;
and/or, the conditions for purification by Sephadex gel column chromatography are as follows: the sample is wet loaded in a pre-packed column in 20% ethanol in water, and then gradiently eluted using a mixed solution of ethanol and water with a volume ratio of 10:2, 10:3, 10:4, 10:5, and 10:10; the volume/weight ratio of eluent to crude compound of formula I for each volume ratio is 500 ml:1 g.

The present invention also provides the use of the compound mentioned above, or a crystal form thereof, or a salt thereof, or a stereoisomer thereof, or a solvate thereof, or a hydrate thereof, or a prodrug thereof for the manufacture of a medicament against herpes simplex virus type I (HSV-I); preferably, the drug is that inhibiting the replication of HSV-I and directly inactivating the virus.

The present invention also provides the use of the compound mentioned above, or a crystal form thereof, or a salt thereof, or a stereoisomer thereof, or a solvate thereof, or a hydrate thereof, or a prodrug thereof for the manufacture of a medicament for the prevention and/or treatment of keratitis; preferably, the keratitis is viral keratitis;
more preferably, the viral keratitis is HSV-I viral keratitis.

The present invention also provides a pharmaceutical preparation, which is formed by a compound mentioned above, or a crystal form thereof, or a salt thereof, or a stereoisomer thereof, or a solvate thereof, or a hydrate thereof, or a prodrug thereof, as active ingredients, together with a pharmaceutically acceptable excipients or adjuvant ingredients;
preferably, the pharmaceutical preparation is an external preparation;
more preferably, the external preparation is eye drops, eye ointments, creams, gels, films, and paints.

Compared with the prior art, the beneficial effects of the present invention are:

The present invention provides a biflavone compound, which has excellent inhibitory activities against HSV-I, and displays significant effects on virus replication and direct inactivation in a dose-dependent manner; the compound of the present invention can effectively prevent and/or treat viral keratitis caused by HSV-I. Moreover, the compound of the present invention has good water solubility and low toxicity, and can be made into external preparations against HSV-I, such as eye drops, eye ointments, as well as ointments, creams, gels, films, paints and the same for external use, which have good safety and broad application prospects.

For the definition of terms used in the present invention: unless defined otherwise, the initial definition provided for the group or term herein applies to the group or term of the whole specification; for the terms that are not specifically defined herein, they should have the same meaning as commonly understood by one of ordinary skill in the art to which the disclosure belongs.

In the present invention, "salts" refers to "pharmaceutically acceptable salts", and the term "pharmaceutically acceptable" refers to a carrier, transporter, diluent, excipient, and/or formed salts are usually chemically or physically compatible with other components constituting a pharmaceutical preparation and biologically compatible with the receptor.

The term "salt" and "pharmaceutically acceptable salt" refer to an acidic and/or basic salt formed by combining a compound or its stereoisomer with inorganic and/or organic acids and/or bases, as well as zwitterionic salts (inner salts) and quaternary ammonium salts, such as alkyl ammonium salts. These salts can be directly obtained during the final separation and purification of the compound. It can also be obtained by mixing a compound or its stereoisomer with a certain amount of acid or base (such as equivalency). These salts may form precipitates in a solution and be collected by filtration, or recovered after evaporation of solvents, or prepared by freeze-drying after reaction in an aqueous medium. In the present invention, the salt can be a compound's hydrochloride, sulfate, citrate, benzenesulfonate, hydrobromate, hydrofluorate, phosphate, acetate, propionate, succinate, oxalate, malate, succinate, fumarate, maleate, tartrate, or trifluoroacetate.

One or more compounds of the present invention can be used in combination with each other, or alternatively, the compound of the present invention can be used in combination with any other active agent. If a group of compounds is used, these compounds can be administered to a subject simultaneously, separately, or sequentially.

Obviously, based on the above content of the present invention, according to the common technical knowledge and the conventional means in the field, other various modifications, alternations, or changes can further be made, without department from the above basic technical spirits.

With reference to the following specific examples of the embodiments, the above content of the present invention is further illustrated. But it should not be construed that the scope of the above subject matter of the present invention is limited to the following examples. The techniques realized based on the above content of the present invention are all within the scope of the present invention.

DESCRIPTION OF FIGURES

FIG. 16. Staining results by a plaque assay method (n=3).

EXAMPLES

Unless otherwise specified, the raw materials and equipment used in the specific examples of the present invention are known products obtained by purchasing those commercially available.

1. The Instrument, Test Drug, Sample, and HPLC Detection Conditions Used in the Present Invention Agilent RRLC-6410 triple quadrupole HPLC-MS (USA), Bruker AVII-600 MHz NMR spectrometer, Agilent 1200 semi-preparative HPLC (USA), Agilent 1100 HPLC, and KQ-500E ultrasonic cleaner (Kun Shan Ultrasonic Instruments Co., Ltd).

Ethanol, methanol, formaldehyde, chromatographic silica gel, Sephadex LH-20 and the same are analytical pure or chromatographic pure, and can be obtained from commercially available products.

Compounds for pharmacological experiments:

Compound 1: sodium tectorigenin-5'-sulphonate (Abbreviated as XYW, prepared according to patent CN1594308A, with a purity of >98%);

Compound 2: 8,8"-methylene-di-(sodium tectorigenin-5'-sulphonate) (Abbreviated as di-XYW, compound of the present invention, for the preparation method, see the Example);

Compound 3: sodium 4,7'-diethyltectorigenin-5'-sulphonate (Abbreviated as MJJ-S, prepared according to patent CN106554339B, with a purity of >98%);

Compound 4: sodium 8,8"-methylene-di-(4,7'-diethyltectorigenin-5'-sulphonate) (Abbreviated as di-MJJ-S, the control compound of the present invention, for the preparation method, see the Comparative Example).

The structures of compounds 1-4 are shown in the following:

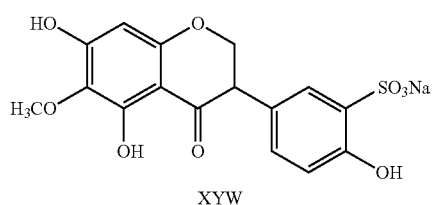

XYW

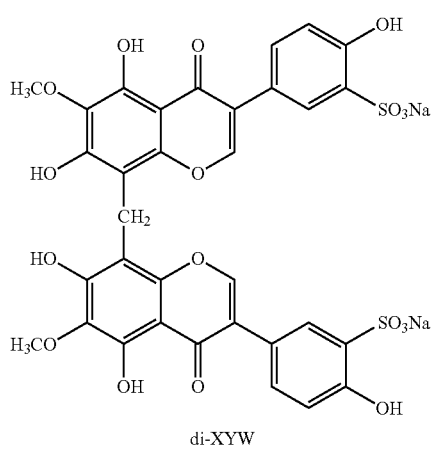

di-XYW

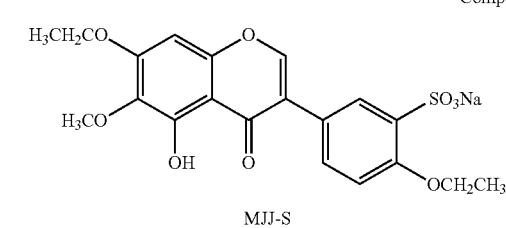

MJJ-S

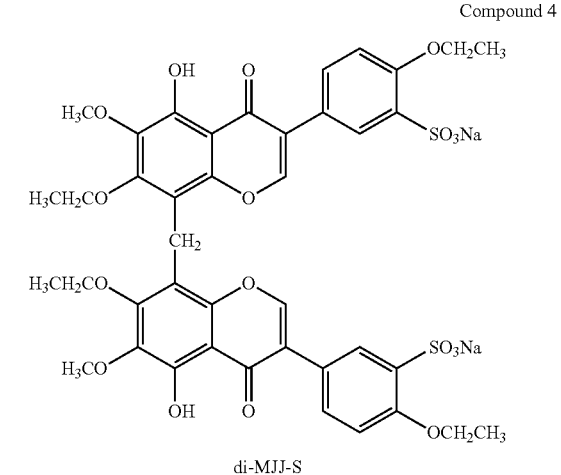

di-MJJ-S

HPLC Detection Conditions:
Chromatographic column: Welch XB-C18 (4.6 mm×150 mm, 5 μm);
Mobile phase: mobile phase A is anhydrous methanol, and mobile phase B is 0.02 mol/L sodium dihydrogen phosphate buffer (preparation method: 3.12 g of sodium dihydrogen phosphate dihydrate is dissolved in 1000 ml of water, and then the pH of the solution is adjusted to 3.0 with phosphoric acid); gradient elution (0 min, 40% A; 20 min, 70% A; 25 min, 70% A);
flow rate: 1.0 ml/min;
column temperature: 35° C.;
detection wavelength: 268 nm;
injection volume: 10 μl.

Comparative Example. Preparation of di-MJJ-S

Figure 1:
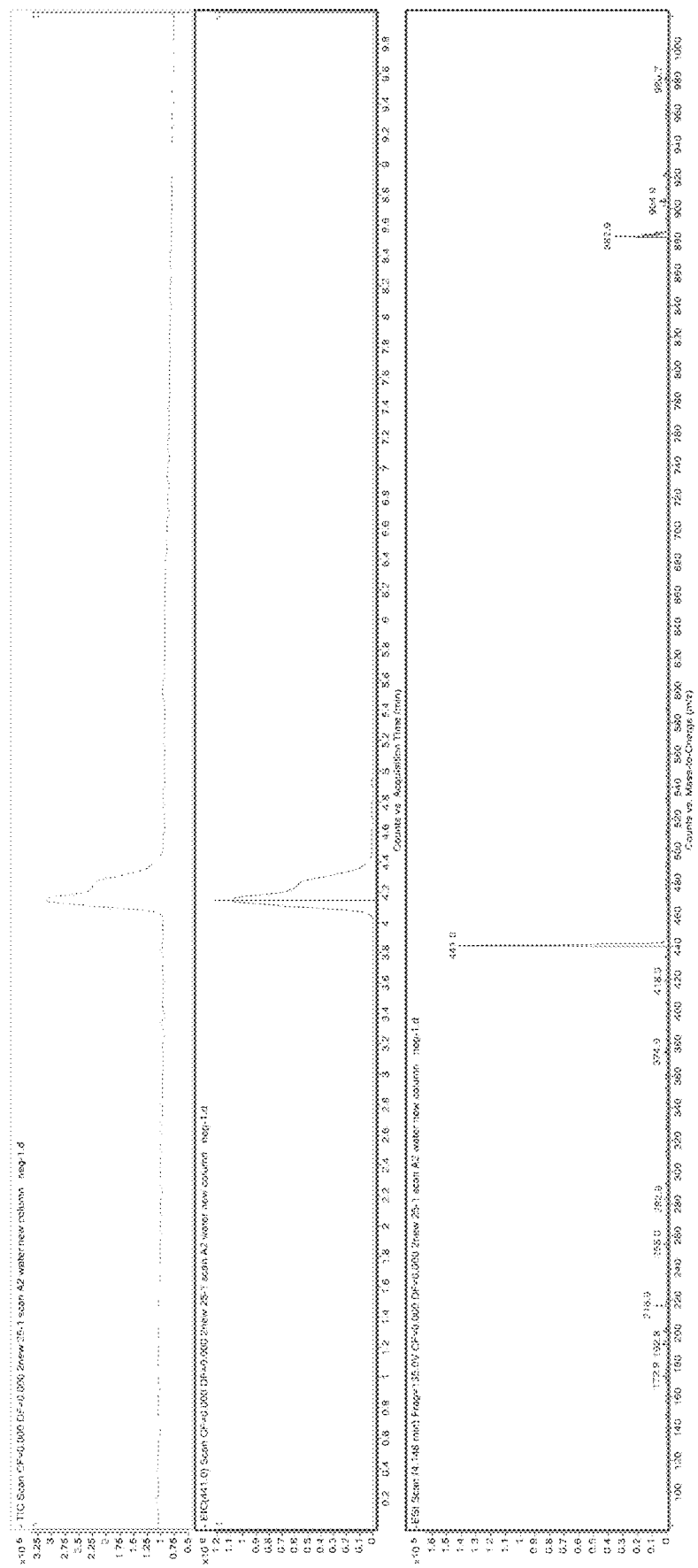
FIG. 1. HPLC-MS of compound 4 (sodium 8,8"-methylene-di-(4,7'-diethyltectorigenin-5'-sulphonate) (Di-MJJ-S).

MJJ-S (1.0 g) was dissolved in 10 ml of water (by heating in a water bath), to which was added 10 ml of formaldehyde solution, and then the mixture was allowed to react in a water bath for 10 hours. The reaction solution was taken out, and the solvent was recovered under reduced pressure at 80° C. The residue was dried under reduced pressure in a $P_2O_5$ dryer, and then recrystallized in a mixed solvent of methanol:water (7:3, v/v) to obtain 0.7 g of di-MJJ-S (compound 4). HPLC-MS indicated that the molecular ion peak of di-MJJ-S is located at m/z 928, confirming that it is di-MJJ-S. Its HPLC-MS is shown in FIG. 1.

Example 1. Preparation of Crude Di-XYW Compound of the Present Invention

Figure 2:
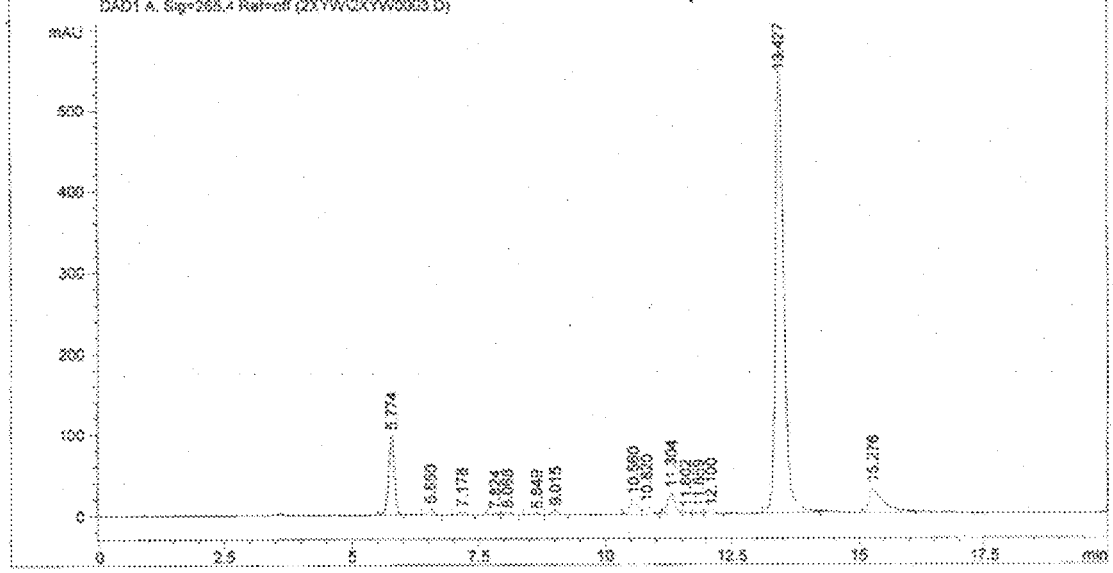
FIG. 2. HPLC of the crude product of the di-XYW compound prepared in Example 1.

To 50.0 g of compound XYW, was add 250 ml of boiling water, and then the mixture was dissolved with aid of ultrasound, followed by addition of formaldehyde (250 ml). The solution was mixed well and heated under reflux in a water bath for 10 hours (using silica gel GF254 TLC to detect the reaction, with a mixed solution of chloroform:methanol:formic acid (in a volume ratio of 10:3:0.1) as the developing system). The reaction solution was moved out, and the solvent was recovered under reduced pressure at 80° C. The residue was dried under reduced pressure in a $P_2O_5$ dryer, to obtain 50.5 g of crude di-XYW compound as a gray white dry powder. The content of compound di-XYW was quantified as 73.94% by the area normalization method. The HPLC is shown in FIG. 2.

Example 2. Preparation of Crude Di-XYW Compound of the Present Invention

Figure 3:
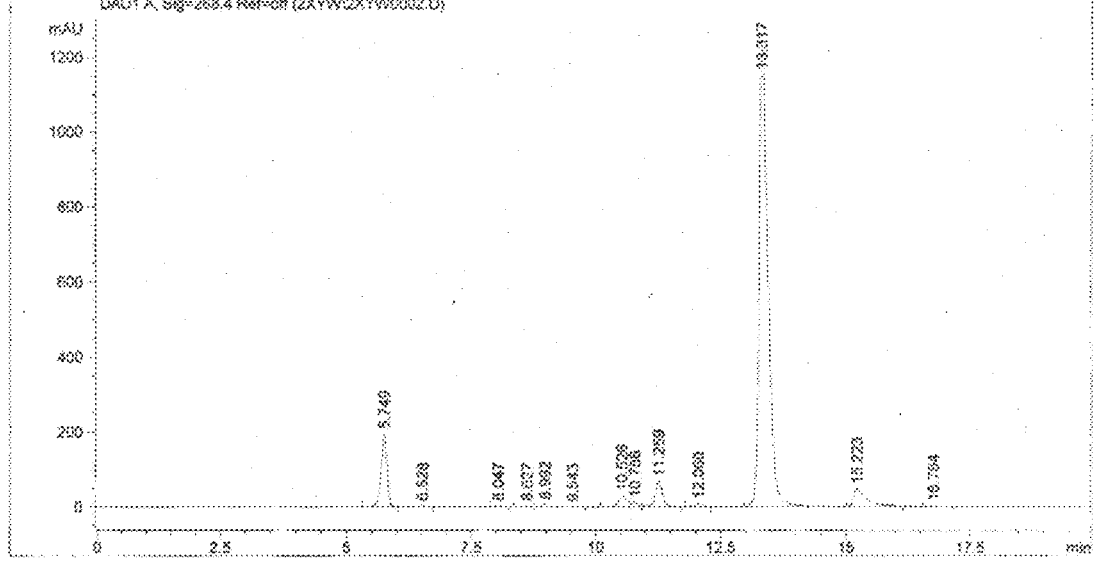
FIG. 3. HPLC of the crude product of the di-XYW compound prepared in Example 2.

To 50.0 g of compound XYW, was add 500 ml of formaldehyde, and then the solution was mixed well and heated under reflux in a water bath for 8 hours (using silica gel GF254 TLC to detect the reaction, and a mixed solvent of chloroform:methanol:formic acid (in a volume ratio of 10:3:0.1) was used as the developing system). Subsequently, the reaction solution was moved out, and the solvent was recovered under reduced pressure at 80° C. The residue was dried under reduced pressure in a $P_2O_5$ dryer, to obtain 50.5 g of crude di-XYW compound as a gray white dry powder. The content of compound di-XYW was determined as 79.16% by the area normalization method. The HPLC is shown in FIG. 3.

Example 3. Purification of Di-XYW Compound According to the Present Invention

Figure 4:
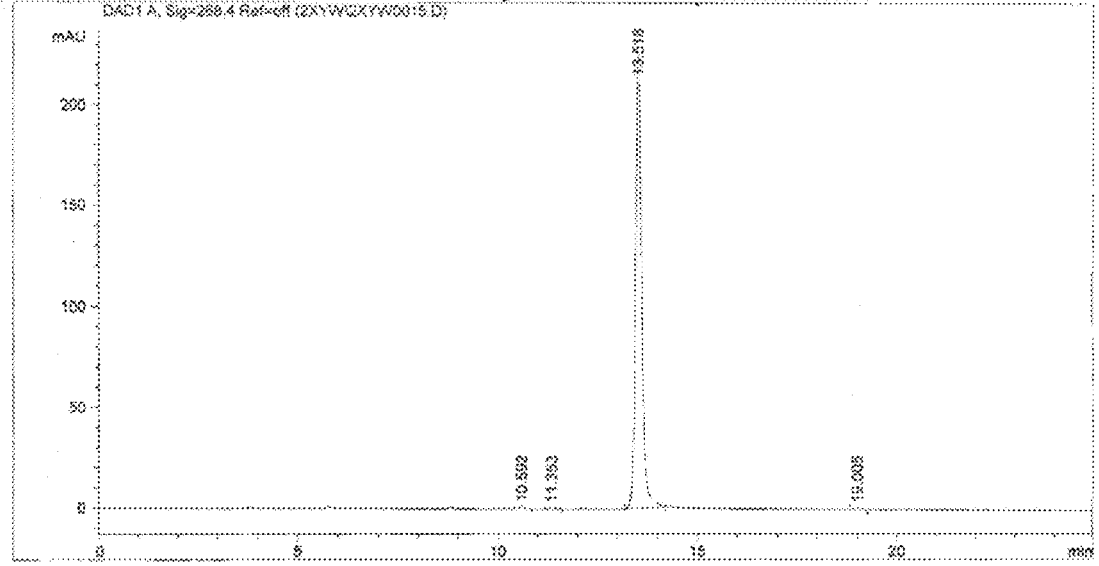
FIG. 4. HPLC of the di-XYW compound prepared in Example 3.

Using a mixed solution of methanol and water (1:1, v/v) as the solvent, the crude di-XYW compound (100 mg) obtained in Example 2 was diluted into a solution with a concentration of 10 mg/ml, and then purified by HPLC. The preparative column was packed with octadecylsilane bonded silica gel, the column temperature was set at room temperature, and the mobile phase was consisted of methanol:water (30:70, v/v), with a flow rate of 10 ml/min. Di-XYW peaks were collected. The solvent was recovered under reduced pressure at 60° C., and then the residue was dried in vacuum, to obtain 36.1 mg of di-XYW compound. The content of di-XYW compound was determined as 98.50% by the HPLC area normalization method. The HPLC is shown in FIG. 4.

Example 4. Purification of Di-XYW Compound According to the Present Invention

Figure 5:
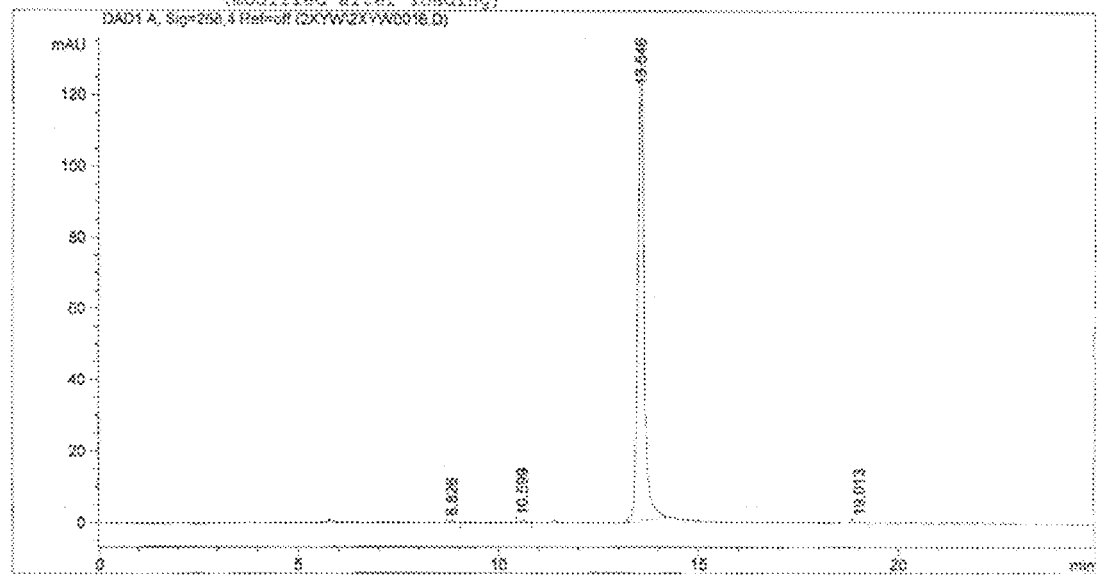
FIG. 5. HPLC of the di-XYW compound prepared in Example 4.

The crude di-XYW compound (1.0 g) obtained in Example 2 was dissolved in 5 ml of boiling water with aid of ultrasound, and then mixed with 10 g of 80-mesh silica gel, followed by drying and grinding, to obtain the sample for column chromatography, which was chromatographed over a 200-300 mesh silica gel column. The sample was loaded on the top of the column, in which silica gel was wet packed in chloroform (hollow glass column, diameter 5-6 cm, column height 80 cm). The column was gradiently eluted with the mixed solvent of chloroform and methanol (the volume ratios of chloroform and methanol were 10:1, 5:1, 2:1, and 1:1). The amount of chloroform-methanol solution used for each volume ratio was 500 ml, and the eluent was collected (50 ml for one portion). The eluents of portions 25-28 were combined, and then the solvent was recovered under reduced pressure at 60° C., and then the residue was dried in vacuum, to obtain 0.52 g of di-XYW compound. The content of di-XYW compound was determined as 98.75% by the HPLC area normalization method. The HPLC is shown in FIG. 5.

Example 5. Purification of Di-XYW Compound According to the Present Invention

Figure 6:
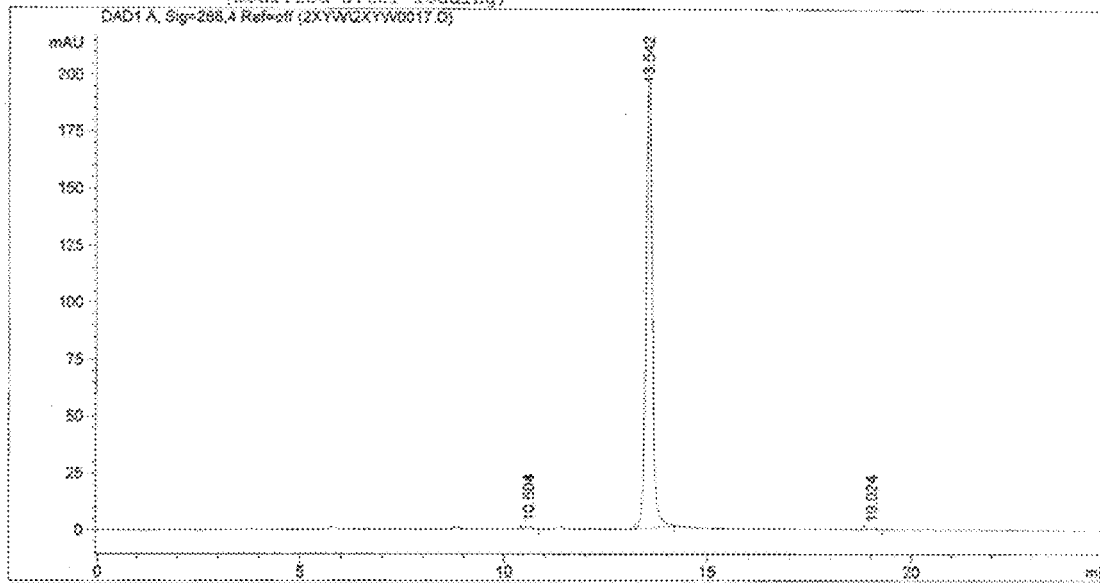
FIG. 6. HPLC of the di-XYW compound prepared in Example 5.

The crude di-XYW compound (10.0 g) obtained in Example 2 was dissolved in 20 ml of boiling water with aid of ultrasound, and then mixed with 20 g of silica gel (100 mesh), followed by drying and grinding, to obtain the sample for column chromatography, which was chromatographed over a 10-40 m silica gel for TLC (hollow glass column, diameter 6-7 cm, column height 100 cm). The column was eluted with the mixed solvent of chloroform and methanol (100:30, v:v). After completion of the development, silica gel was poured out from the glass column in a fume hood, cut into 25 equal parts, and then parts 18-20, numbered with a beginning from the sample location, were combined, followed by eluting with methanol. The solvent was recovered under reduced pressure at 60° C., and then the residue was dried in vacuum, to obtain 5.8 g of di-XYW compound. The content of di-XYW compound was determined as 98.98% by the HPLC area normalization method. The HPLC is shown in FIG. 6.

Example 6. Purification of Di-XYW Compound According to the Present Invention

Figure 7:
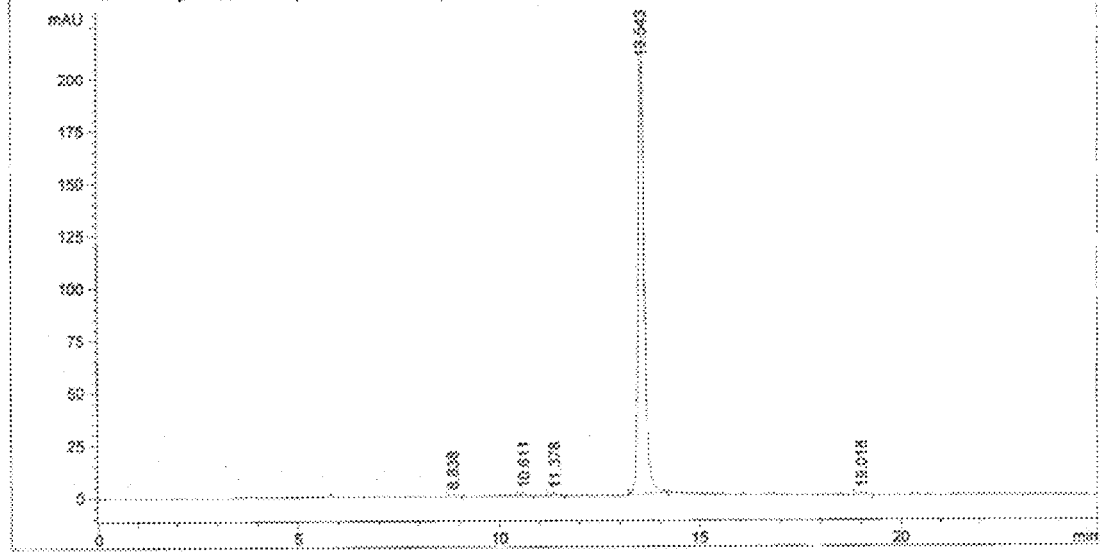
FIG. 7. HPLC of the di-XYW compound prepared in Example 6.
Figure 8:
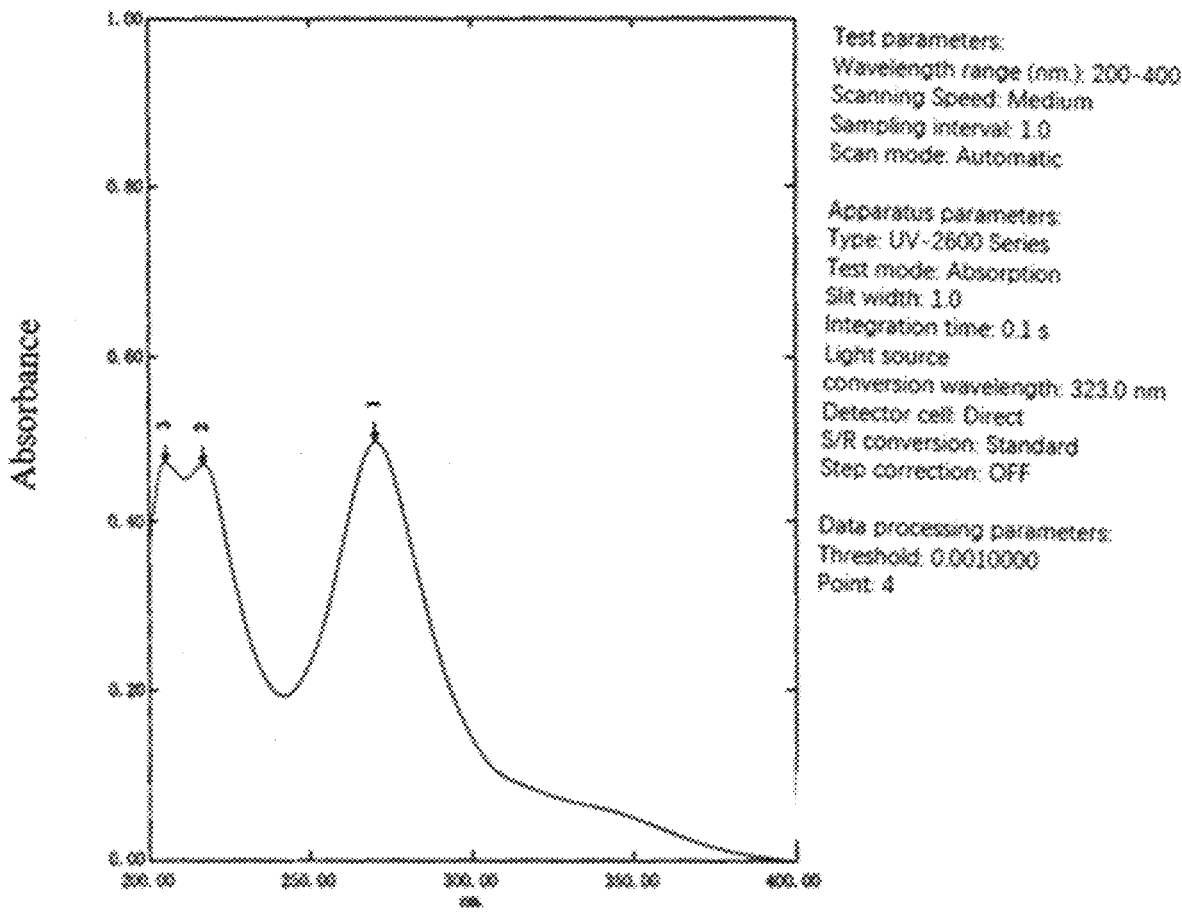
FIG. 8. The UV spectrum of the compound according to the present invention.
Figure 9:
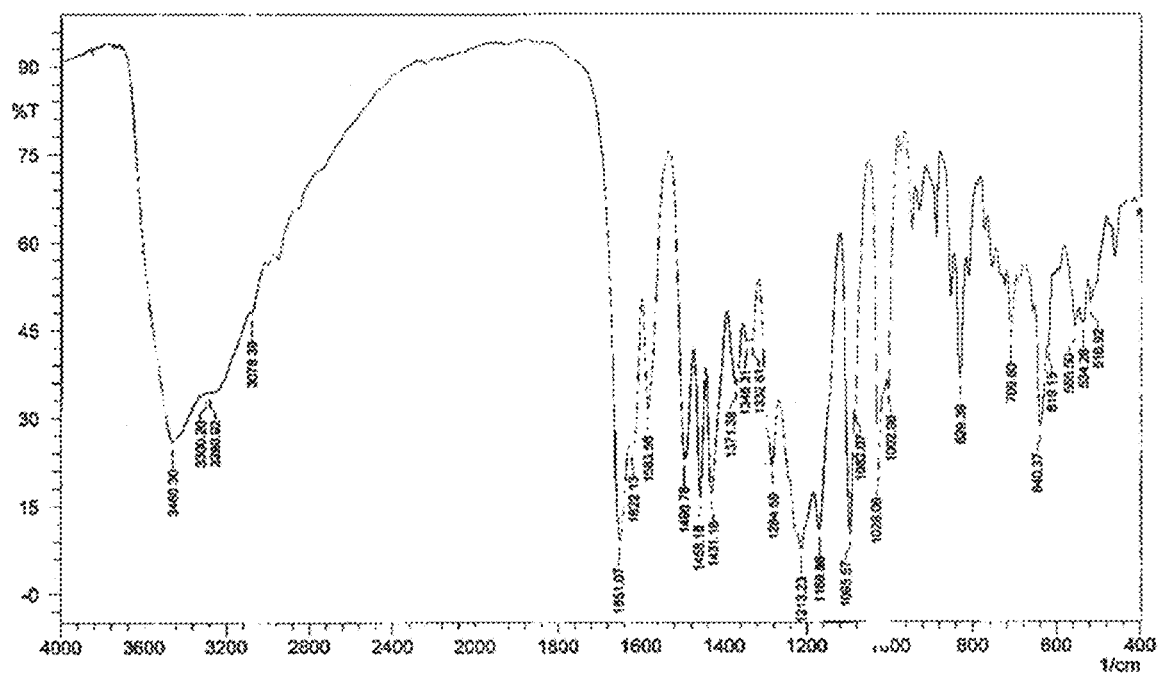
FIG. 9. The IR spectrum of the compound according to the present invention.
Figure 10:
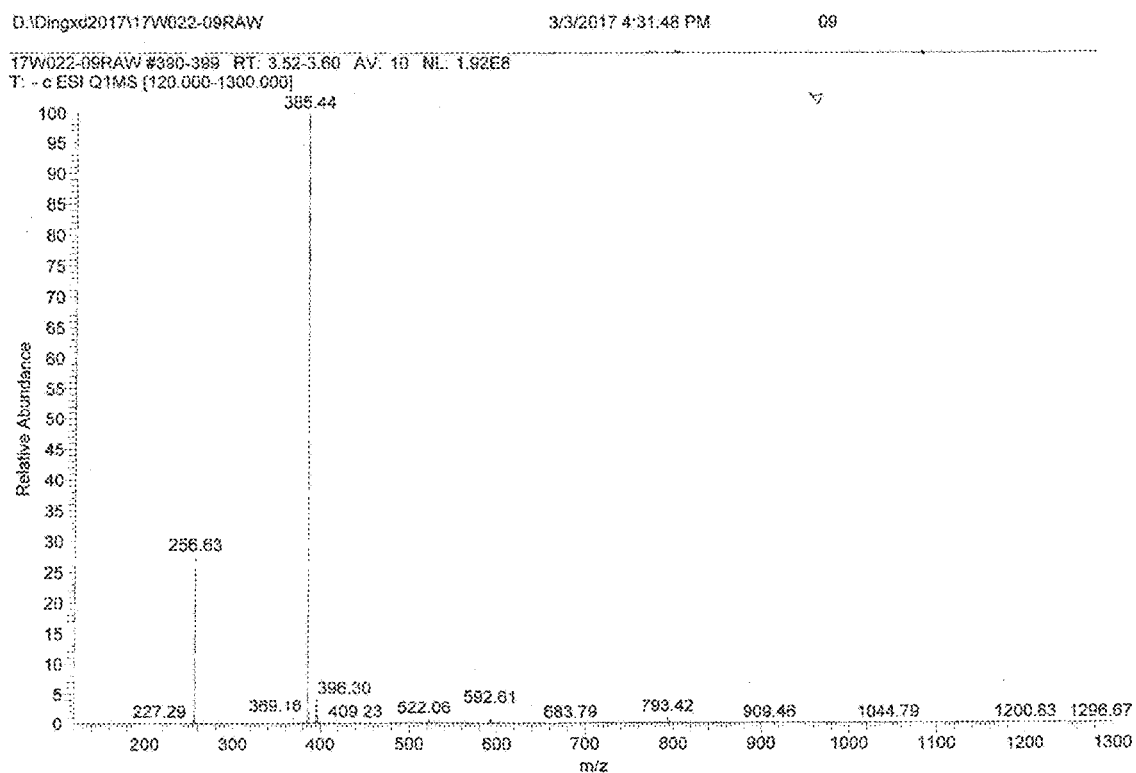
FIG. 10. The MS of the compound according to the present invention.
Figure 11:
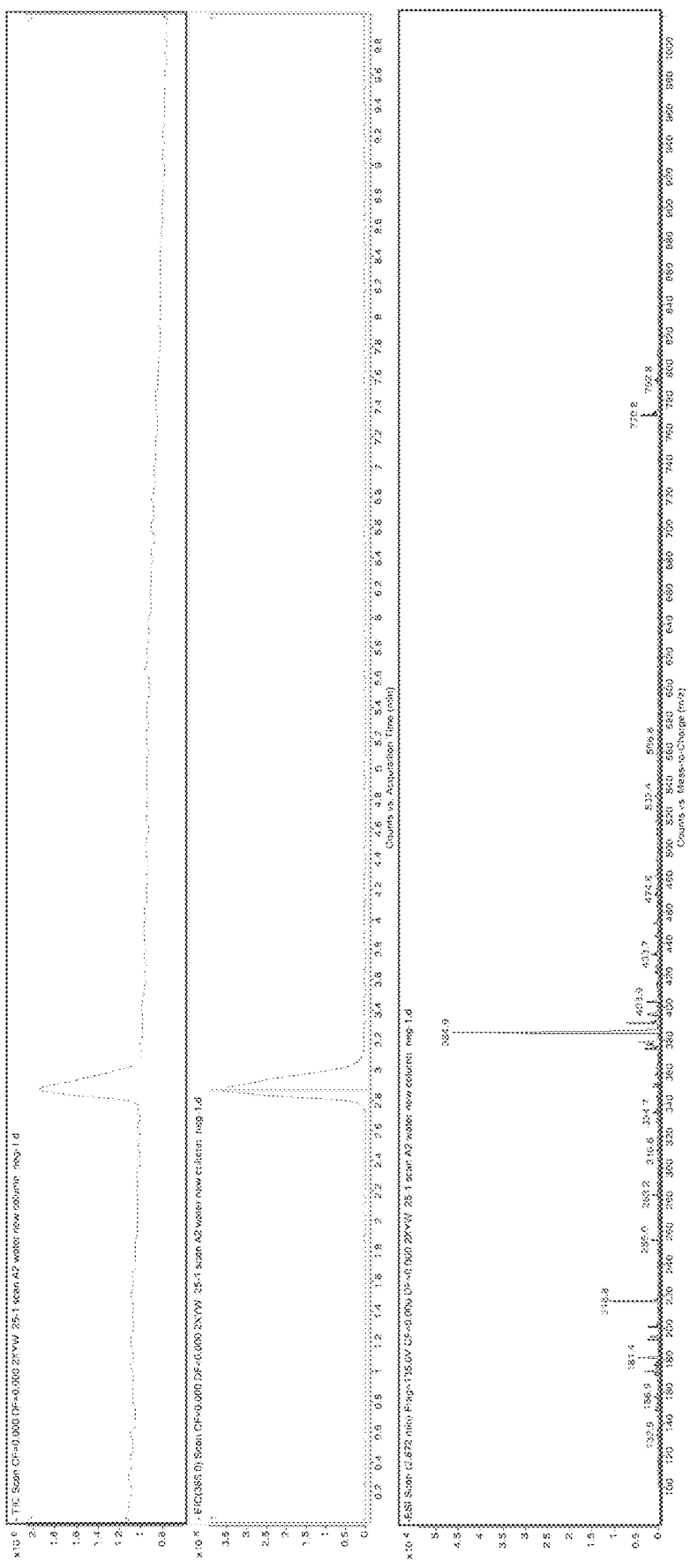
FIG. 11. HPLC-MS of the compound according to the present invention.
Figure 12:
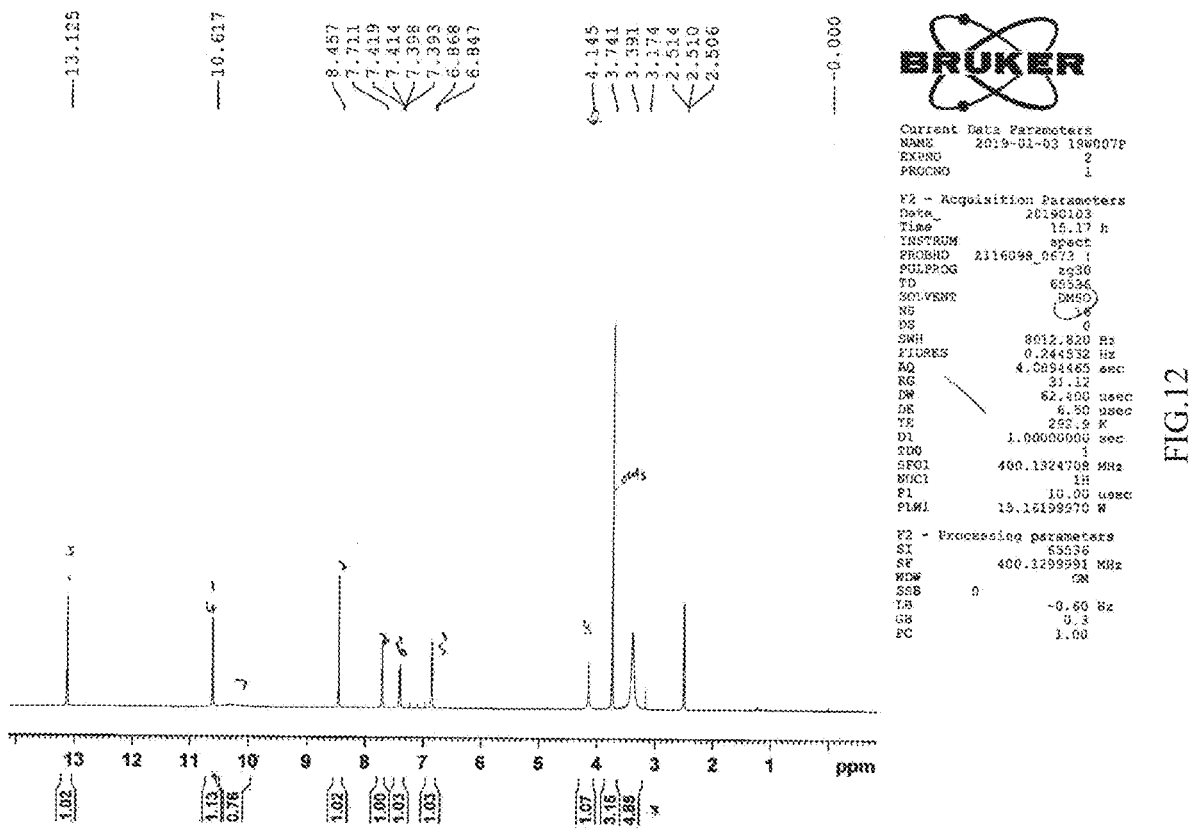
FIG. 12. The $^1$H NMR spectrum of the compound according to the present invention.
Figure 13:
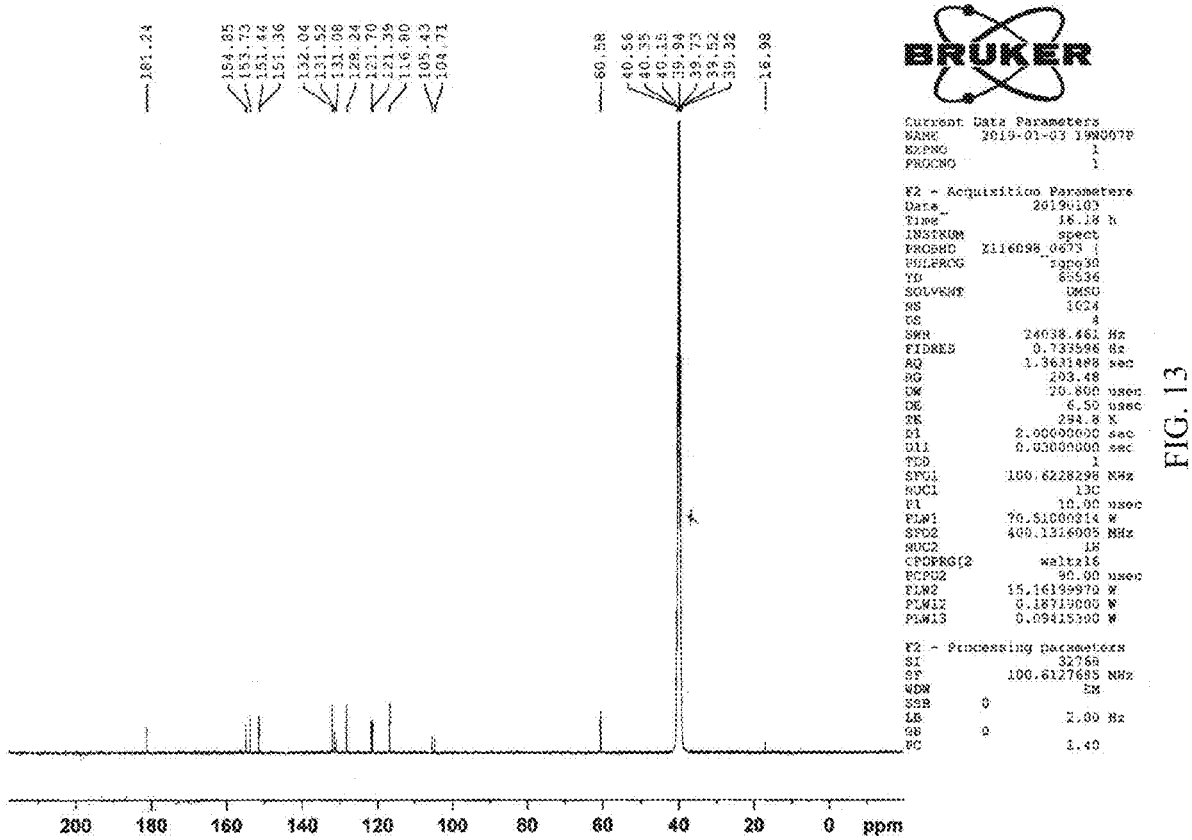
FIG. 13. The $^{13}$C NMR spectrum of the compound according to the present invention.

The crude di-XYW compound (1.0 g) obtained in Example 2 was dissolved in 5 ml of 20% EtOH aqueous solution with aid of ultrasound, and then filtered, to obtain the sample for column chromatography, which was chromatographed over a Sephadex LH-20 column. The sample was loaded on the top of the column, in which Sephadex LH-20 was wet packed in 20% EtOH aqueous solution (hollow glass column, diameter 5-6 cm, column height 80 cm). The column was gradiently eluted with the mixed solvent of EtOH and water (the volume ratios of EtOH and water were 10:2, 10:3, 10:4, 10:5, and 10:10). The amount of EtOH-water solution used for each volume ratio was 500 ml, and the eluent was collected (50 ml for one portion). The eluents of portions 30-35 were combined, and then the solvent was recovered under reduced pressure at 60° C., and then the residue was dried in vacuum, to obtain 0.45 g of di-XYW compound. The content of di-XYW compound was determined as 98.15% by the HPLC area normalization method. The HPLC is shown in FIG. 7.

Example 7. Structural Characterization of Di-XYW Compound According to the Present Invention The UV and IR spectra were measured by the Analysis and Testing Center, Sichuan Academy of Chinese Medicine Sciences; HPLC-MS was performed by our laboratory. All other spectra were obtained by the Analysis and Testing Center of Sichuan University.

The UV, IR, MS, HPLC-MS, $^1$H NMR, and $^{13}$C NMR spectra of the di-XYW compound prepared in Example 5 are shown in FIGS. 8-13, respectively. The compound was characterized as 8,8"-methylene-bis-tectorigenin-5'-sulphonate sodium (di-XYW), with the following structure:

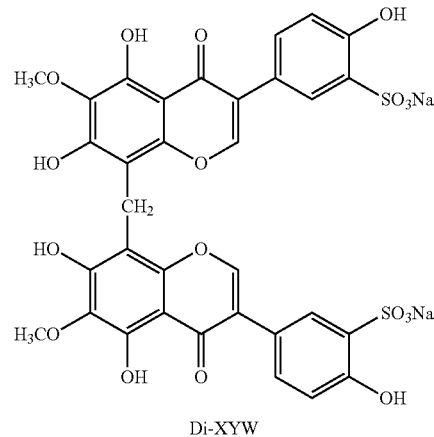

Di-XYW

Example 8. Formulation of the Pharmaceutical Preparation Comprising the Di-XYW Compound of the Present Invention The compound (di-XYW) of the present invention, together with a pharmaceutically acceptable carrier, can be made into different pharmaceutical preparations, e.g. ophthalmic preparations such as eye drops and eye ointments, as well as topical preparations such as ointments, creams, gels, films, and paints.

1. Preparation of Eye Drops:

[Formula] 5 g of di-XYW compound, 10.5 g of boric acid, 2.9 g of borax Dilution with distilled water to 1000 ml

[Preparation] To boric acid and borax, was added 900 ml of distilled water, and then the solution was heated to dissolve, followed by addition of di-XYW compound. The resultant solution was heated and boiled for additional 10 minutes, and then cooled. After that, the solution was filtered using a sintered glass filter (No. 6) or a millipore filter (0.22 μm filter membrane), and then the filtrate was diluted with sterilized distilled water to 1000 ml. The solution was stirred well, packed separately, and sterilized with steam at 100° C. for 30 minutes, to obtain eye drops.

2. Preparation of Eye Ointments:

[Formula] 5 g of di-XYW compound, 95 g of liquid paraffin, 100 g of anhydrous lanolin, adding yellow vaseline to 1000 g

[Preparation] The di-XYW ultra-fine powder was placed in a mortar, to which was added an appropriate amount of sterilized and cooled liquid paraffin, and then the mixture was ground into a fine paste, and passed through a 100-mesh sieve. Subsequently, the sterilized and filtered mixture of lanolin and yellow vaseline was gradually added, and the mixture was mixed thoroughly.

3. Preparation of Creams:

[Formula] 5 g of di-XYW compound, 170 g of stearic acid, 100 g of glyceryl monostearate, 130 g of white vaseline, 15 g of sodium laurylsulfonate, 100 g of glycerol, 1.5 g of ethyl p-hydroxybenzoate, adding distilled water to 1000 g.

[Preparation] O/W type cream was prepared by emulsification.

4. Preparation of Gels:

[Formula] 5 g of di-XYW compound, 10 g of cabomer 940, 10 g of triethanolamine, 0.5 g of ethyl p-hydroxybenzoate, 10 g of glycerol, adding distilled water to 1000 g.

[Preparation] Ethyl p-hydroxybenzoate and carbomer 940 were added to distilled water, and then heated and dissolved in a 70° C. water bath. After cooling, glycerol and di-XYW compound were added and dissolved. Finally, triethanolamine was added and stirred well to obtain the gels.

5. Preparation of Films:

[Formula] 1 g of di-XYW compound, 2 g of PVA05-88, 2 g of glycerol, adding distilled water to 30 ml.

[Preparation] The films were made according to the general method.

6. Preparation of Paints:

[Formula] 5 g of di-XYW compound, 30 g of dibutyl phthalate, 130 g of poly(vinyl formalacetal), 100 g of acetone, an appropriate amount of 70% ethanol, in a total of 1000 g.

[Preparation] The paints were made according to the general method.

The beneficial effects of the present invention were demonstrated by following Experimental Examples.

Experimental Example 1: In Vitro Anti-HSV-I Activity of the Di-XYW Compound According to the Present Invention I. Experimental Objective 1. The cytotoxic activities of compounds 1-4 against African green monkey kidney cells (Vero) were investigated, as well as the half toxic concentrations ($TC_{50}$) and the highest non-toxic concentrations of compounds 1-4 against Vero cells were calculated.

2. An in vitro model of Herpes simplex virus type I (HSV-I) was established, the viral titer ($TCID_{50}$) that causes the pathological changes for half of the cells was calculated, and then compounds 1-4 were preliminarily assayed to find the active compounds against HSV-I.

3. The inhibitory activities of compounds 1-4 against the pathological changes of Vero cells induced by HSV-I were investigated by cytopathic effect (CPE) assay and plaque reduction assay, and the half effective concentration ($IC_{50}$) and selection index (SI) were calculated.

4. The CPE method was used to preliminarily study the anti-HSV-I action mode of the selected active compounds.

II. Experimental Reagents and Instruments

1. Experimental reagents: MEM incomplete culture medium (Jiangsu KeyGEN BioTECH Corp., Ltd., lot number: 20210510); phosphate buffer (Jiangsu KeyGEN BioTECH Corp., Ltd., lot number: 20210323); fetal bovine serum (ExCell Bio, lot number 42Q9281K); TrypLE select (lx) (Gibco, lot number 2279546); cell culture grade DMSO (Dimethyl Sulfide) (SIGMA, lot number: RNBJ2585); HEPES (1M) (Gibco, lot number 2192897); 4% para-formaldehyde fixative (Beyotime, lot number: No. 06092020200909); CCK-8 (DojinDO, lot number: PH632).

2. Experimental samples: Compounds 1, 2, 3, and 4 were used as the experimental samples. Compound 2, i.e. the compound of the present invention (di-XYW), was the sample obtained in Example 5, with a content of 98.98%.

3. Experimental instrument: $CO_2$ cell incubator (SANYO, model: MCO-18AIC (UV)); clean bench (AIRTECH, model: SW-CJ-2FD); fluorescent inverted microscope (Zeiss, model: Observer. AI); automatic microplate spectrophotometer (Molecular Devices, model: Spectra Max 190).

4. Cells and viral strains: African green monkey kidney cells (Vero) were purchased from the cell bank of the China Center for Type Culture Collection of the Chinese Academy of Sciences (CCTCCCAS). Herpes Simplex Virus Type I (HSV-I) MacIntype strains were obtained from ATCC, USA.

III. Experimental Content

1. Virus amplification: Vero cells were successfully developed to cover the bottom of the cell culture dish, in which the virus was grown. The cells were inoculated with HSV-I virus solution, and then cultured in a cell incubator for 1 h, so that the virus was adsorbed into the cells. After incubation, the cell maintenance solution was displaced, followed by cultivation for additional 3-4 days. When >90% of the cells show pathological changes, the culture dish was frozen and thawed for 2-3 times. The virus solution was collected and filtered, to remove the cell fragments, and then the solution was separately packed, which were stored in a −80° C. refrigerator for future use.

2. Virulence Test:

(1) Cytopathic effect (CPE) assay for $TCID_{50}$: Vero cells were inoculated into a 96-well plate and grew into a monolayer the next day. Then, the virus solution was diluted at a ratio of 1:10 from $10^{-1}$ to $10^{-9}$ and added to each well for 1 hour of incubation. At the same time, a normal control group was set up. After incubation, the cell maintenance media was displaced, and the cells were continually cultivated in a cell incubator. The cytopathic effect (CPE) was observed daily. After 4-5 days, the cytopathy in each well no longer developed. The number of positive wells in each group was recorded, and the $TCID_{50}$ value was calculated using the Reed-Muench method.

(2) Determination of viral titer PFU using plaque assay: Vero cells were seeded into a 24-well plate and grew into a monolayer the next day. Then, the virus solution was subjected to double dilution, to obtain 7 concentrations, and then added to each well for 1 hour of incubation. After that, 0.8% agarose cover solution for maintenance of cells was replaced, and the cells were cultivated for additional 72 hours, followed by fixing with 4% paraformaldehyde, staining with crystal violet solution, washing, and drying. The plaque was counted to calculate the viral titer (PFU).

$$\text{Viral titer }(PFU/\text{ml}) = \text{Dilution degree} \times \frac{P1 + P2 + \ldots + Pn}{n} \times \frac{1}{V};$$

wherein, P=the plaque number in each well of the culture plate for the specific dilution, n=the number of wells inoculated with this dilution, and V=the amount of virus inoculated for each well (ml).

3. Cytotoxic assay of tested drugs against Vero cells: Vero cells were seed in a 96 well plate at $3\times10^4$ cells/well. The next day, after growing into a monolayer, the test drug was diluted to obtain 8-9 concentrations and added to each well. Meanwhile, a normal control group was established, with 4 replicate wells for each group. After 72 hours, the toxicity of the test drug to Vero cells was measured using CCK-8 assay, and the highest non-toxic concentration and half toxic concentration ($TC_{50}$) of the drug on the cells were calculated.

4. In Vitro Pharmacodynamic Study of the Tested Drug Against HSV-I (1) Determination of the inhibitory activities of the test drugs on pathological changes of Vero cells induced by HSV-I using the cytopathic effect (CPE) assay: Vero cells were seeded in a 96-well plate and grew into a monolayer the next day. $100TCID_{50}$ HSV-I was added to infect cells, and then the cell maintenance solution containing different concentrations of the test drug was replaced, and a cell control group was included. The cells were cultured in an incubator for 72 hours. Then, the inhibitory effect of the drug on virus-induced cytopathic changes was measured using the CCK-8 assay, and thus the 50% inhibiting concentration ($IC_{50}$) of the drug was calculated.

(2) Measurement of the inhibitory effect of drugs on the formation of plaque in Vero cells induced by HSV-I using plaque-reduction method: Vero cells were seeded into a 24-well plate and grew into a monolayer the next day. Then, the 100 PFU/0.2 ml virus solution was added to infect the cells, and a cell control group was included. After incubation with the virus, the agarose cover solution for maintenance of cells, containing different concentrations of the test drug, was replaced, followed by cultivation for additional 72 hours. The cell culture was fixed with 4% paraformaldehyde, stained with 1% crystal violet solution, washed, and dried. The plaque was counted to calculate plaque-forming inhibition ratio of the drug.

The plaque-forming inhibition ratio =

$$\frac{\text{(The number of plaques in virus control group} - \text{The number of plaques in drug treatment group)}}{\text{The number of plaques in virus control group}} \times 100\%$$

5. Study on the Action Mode of the Test Drug (1) The inhibitory effect of drugs on HSV-I adsorption: Vero cells were seeded in a 96-well plate and grew into a monolayer, before pretreatment with different concentrations of samples. Then, HSV-I virus solution was added at 100 µl/well, followed by incubation for 1 hour. Finally, the cell maintenance solution was replaced, and the cells were further cultured. After 72 hours, the effect on the adsorption of virus was determined using the CCK-8 method.

(2) The inhibitory effect of drugs on HSV-I replication: Vero cells were seeded in a 96-well plate and grew into a monolayer, before adding HSV-I virus solution at 100 µl/well, followed by incubation for 1 hour. Then, the cell maintenance solution containing different concentrations of sample was replaced, and the cells were further cultured. After 72 hours, the effect on the replication of virus was determined using the CCK-8 method.

(3) The direct inactivation effect of drugs on HSV-I: Vero cells were seeded in a 96-well plate and grew into a monolayer. Different concentrations of samples were respectively mixed with the virus solution, followed by placing at 37° C. for 1 hour. Then, the solution was added the cells, and incubated for 1 hour. Then, the cell maintenance solution was replaced, and the cells were further cultured. After 72 hours, the direct inactivation effects of drugs on HSV-I was determined using the CCK-8 method. Moreover, a virus control group was set up.

6. Data statistics and analysis: The results were expressed as mean±standard deviation ($\bar{x}\pm s$), and the data were analyzed using SPSS 19.0 statistical software. The inhibition rate was calculated using probit regression method; the comparison between the two groups was performed using t-test, in which $P<0.05$ represented the difference was statistically significant.

IV. Experimental Results

1. HSV-I Infection Inducing Pathological Changes of Vero Cells

Figure 14:
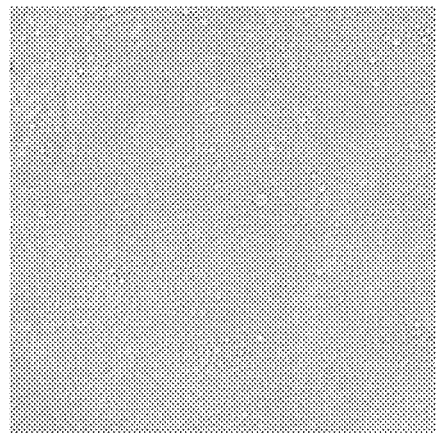
FIG. 14. Vero cells in normal state.
Figure 15:
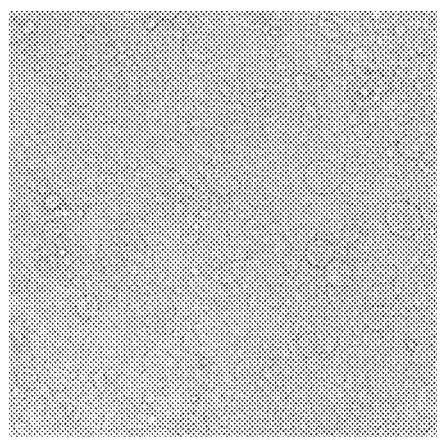
FIG. 15. Diseased Vero cells after inoculation with HSV-I.

FIG. 14 shows the normal state of Vero cells, while FIG. 15 shows the pathological changes of Vero cells after infection with HSV-I.

Figure 16:
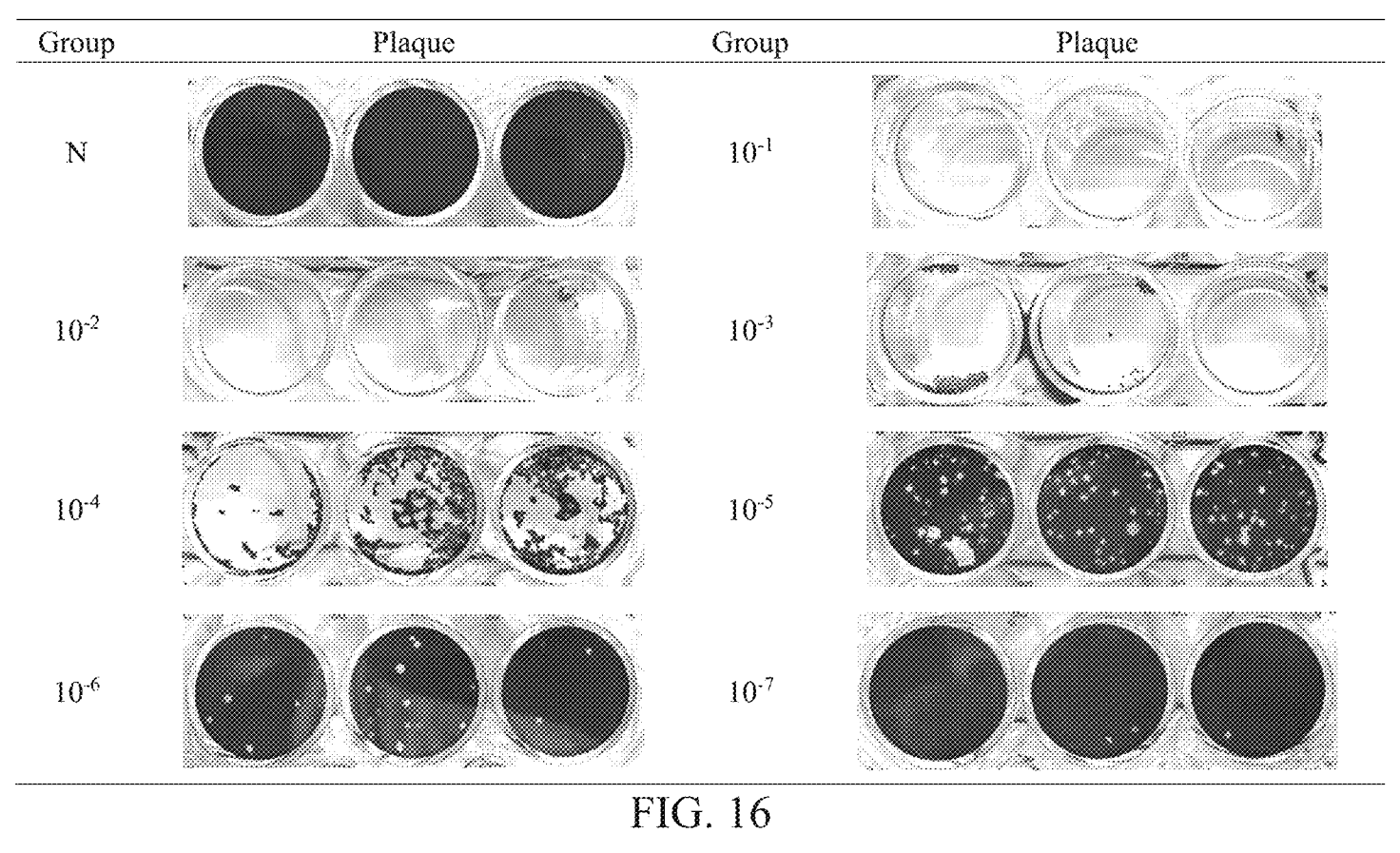

2. Determination of HSV-I Viral Titer Using the CPE Method and Plaque Assay Method For CPE method, the $TCID_{50}$ value of the virus was calculated to be $10^{-4.4}$ using the Reed-Muench method, as shown in Table 1. The concentration of virus inoculation during the efficacy test was $100TCID_{50}$. For the plaque assay method, the viral titer (PFU) was calculated to be $4\times10^7/0.2$ ml, based on the viral maximum dilution having the countable plaque numbers, as shown in FIG. 16. HSV-I with a titer of 100 PFU was used in the efficacy test.

TABLE 1

Observation and results using CPE.

| Viral dilution | Infection wells | Seeding wells | Observations Positive | Observations Negative | Cumulative value Positive | Cumulative value Negative | infection rate | Infection percentage (%) |
|---|---|---|---|---|---|---|---|---|
| $10^{-1}$ | 12 | 12 | 12 | 0 | 47 | 0 | 47/47 | 100 |
| $10^{-2}$ | 12 | 12 | 12 | 0 | 35 | 0 | 35/35 | 100 |
| $10^{-3}$ | 12 | 12 | 12 | 0 | 23 | 0 | 23/23 | 100 |
| $10^{-4}$ | 9 | 12 | 9 | 3 | 11 | 3 | 11/14 | 78.57 |
| $10^{-5}$ | 1 | 12 | 1 | 11 | 2 | 14 | 2/16 | 12.50 |
| $10^{-6}$ | 1 | 12 | 1 | 11 | 1 | 25 | 1/26 | 3.85 |
| $10^{-7}$ | 0 | 12 | 0 | 12 | 0 | 37 | 0/37 | 0 |

3. Toxicity of the Tested Drug to Vero Cells

After staining with CCK-8 method, cell viability was detected at a wavelength of 450 nm using an enzyme-linked immunosorbent assay (ELISA). By Probit regression in SPSS software, the $TC_{50}$ values of the four samples on Vero cells were calculated to be 390.312 µg·mL$^{-1}$, 1749.982 µg·mL$^{-1}$, 3020.44 µg·mL$^{-1}$, and 11308.7 µg·mL$^{-1}$, respectively, with a respective highest non-toxic concentrations of 1.602 µg·mL$^{-1}$, 382.804 µg·mL$^{-1}$, 3.496 µg·mL$^{-1}$, and 0.864 µg·mL$^{-1}$. The results are shown in Table 2 below.

TABLE 2

The growth inhibition rate (%) of the test drug on Vero cells (starting from the highest solubility, 8-9 concentrations were obtained in 50% dilution).

| Compound 1 (971 µg · ml$^{-1}$) | Compound 2 (1600 µg · ml$^{-1}$) | Compound 3 (2620 µg · ml$^{-1}$) | Compound 4 (390 µg · ml$^{-1}$) |
|---|---|---|---|
| 57.86** | 41.92** | 45.06** | 28.40** |
| 49.99** | 29.02** | 40.80** | 27.54** |
| 42.06** | 11.69** | 36.94** | 26.53** |
| 39.97** | −4.55 | 34.23** | 23.48** |
| 34.95** | 5.46 | 32.36** | 22.02** |
| 28.48** | −4.74 | 27.12** | 18.43** |
| 27.14** | −12.11 | 25.55** | 14.94** |
| 25.37** | −8.20 | 22.06** | 9.42 |
| −1.57 | −13.88 | −0.24 | −23.23 |

Note:
Compared with the normal cell control group,
**P < 0.01,
*P < 0.05.

4. In Vitro Pharmacodynamic Results of Test Drugs Against HSV-I

Among the four samples, compound 2 had lower toxicity, and thus its selectable concentration was higher; the other three compounds had relatively high toxicity, indicating lower selectable concentrations, and therefore, they could not be diluted more. Compounds 1 and 3-4 were diluted in a ratio of 50% based on the highest non-toxic concentration, to provide 3 concentrations for preliminarily studying their in vitro anti-HSV-I activities. Compound 2 was diluted from the highest non-toxic concentration, to obtain 8 or 9 concentrations, as shown in Table 3 below.

In Table 3, compound 1 exhibited a concentration gradient, but due to the narrow concentration range of administration, the effect was not significant. Compounds 3 and 4 had no significant inhibitory effect on HSV-I.

Figure 17:
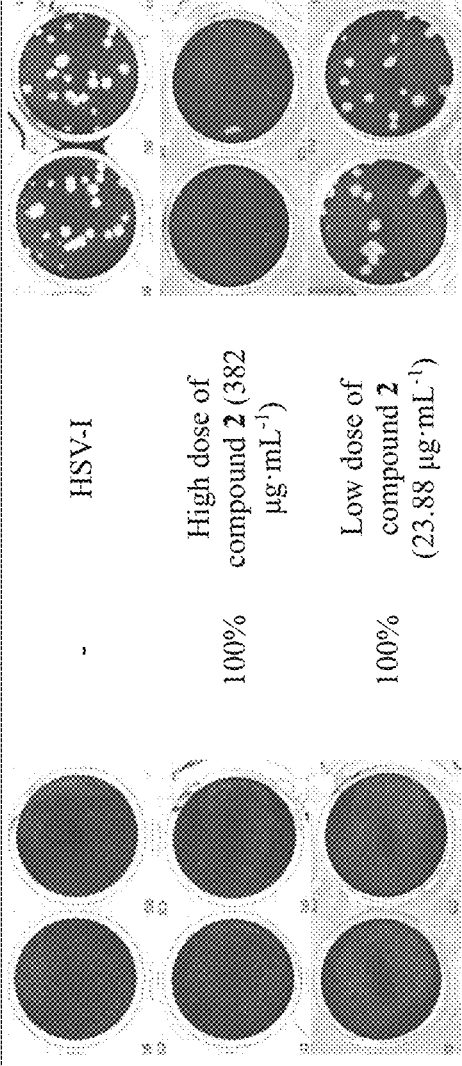
FIG. 17. The inhibition rate of compound 2 against the plaque formation of Vero cells induced by HSV-I.

By observing the experimental results using CPE and plaque reduction methods, it could be seen that compound 2 had a significant inhibitory effect on the cytopathic changes and plaque formation induced by HSV-I, that was dose-dependent. The results are shown in Table 4, Table 5, and FIG. 17. The $IC_{50}$ value of compound 2 was calculated to be 54.488 µg/ml by Probit regression.

By calculating the selection index ($SI=TC_{50}/IC_{50}$), the efficacy of the test drug was evaluated, and the SI value of compound 2 was 32.117.

TABLE 4

The inhibition rate of the test drug on the pathological change of Vero cells caused by HSV-I (n = 6, $\bar{x} \pm s$).

| Group | Dosage (µg/ml) | Average optical density (OD) | Inhibition rate (%) |
|---|---|---|---|
| Normal cell control group | — | 1.11 ± 0.05 | — |
| Viral control group | — | 0.33 ± 0.03 | — |
| Compound 2 | 382.00 | 1.10 ± 0.03 | 99.20** |
|  | 191.00 | 1.06 ± 0.05 | 94.00** |
|  | 95.50 | 0.95 ± 0.04 | 79.87** |
|  | 47.75 | 0.65 ± 0.06 | 40.70** |
|  | 23.88 | 0.44 ± 0.07 | 14.54** |
|  | 11.94 | 0.35 ± 0.05 | 2.87 |
|  | 5.97 | 0.33 ± 0.04 | −0.36 |

Note:
compared with the viral control group,
**P < 0.01.

TABLE 5

Efficacy evaluation of compound 2 against HSV-I (µg/ml).

| Drug | $TC_{50}$ | $IC_{50}$ | SI |
|---|---|---|---|
| Compound 2 | 1749.982 | 54.488 | 32.117 |

5. Study on the Mode of Action of Test Drugs Against HSV-I

By using the CPE method, the mode of action of drugs against HSV-I was studied. The results showed that compound 2 had a significant effect on viral replication and direct inactivation in a dose-dependent manner, but had almost no inhibitory effect on viral adsorption.

TABLE 3

The inhibition rate of compounds 1, 3, and 4 on the pathological changes of Vero cells induced by HSV-I (n = 5, $\bar{x} \pm s$).

| Compounds | Normal control group OD value | Viral group OD value | Concentration 1 OD value | Concentration 1 Inhibition rate (%) | Concentration 2 OD value | Concentration 2 Inhibition rate (%) | Concentration 3 OD value | Concentration 3 Inhibition rate (%) |
|---|---|---|---|---|---|---|---|---|
| Compound 1 | 0.83 ± 0.08 | 0.35 ± 0.01 | 0.37 ± 0.04 | 4.41 | 0.37 ± 0.02 | 3.29 | 0.36 ± 0.03 | 2.26 |
| Compound 3 |  |  | 0.38 ± 0.05 | 6.20 | 0.39 ± 0.10 | 8.65 | 0.37 ± 0.03 | 4.09 |
| Compound 4 | 0.70 ± 0.04 | 0.29 ± 0.05 | 0.32 ± 0.02 | 5.96 | 0.32 ± 0.01 | 6.09 | 0.32 ± 0.01 | 5.99 |

TABLE 6

Research results on the action mode of compound 2 against HSV-I (n = 6, $\bar{x} \pm s$).

| Groups | Dosage (μg/ml) | Effect on viral replication | | Effect on viral adsorption | | Direct inactivation | |
|---|---|---|---|---|---|---|---|
| | | OD value | Inhibition rate (%) | OD value | Inhibition rate (%) | OD value | Inhibition rate (%) |
| Normal control group | | 1.00 ± 0.07 | | 1.03 ± 0.04 | | 1.09 ± 0.03 | |
| Viral control group | | 0.22 ± 0.01 | | 0.19 ± 0.02 | | 0.30 ± 0.02 | |
| Compound 2 | 382.00 | 0.99 ± 0.02** | 98.83 | 0.24 ± 0.06 | 5.39 | 1.08 ± 0.06** | 98.68 |
| | 191.00 | 0.98 ± 0.12** | 98.00 | 0.25 ± 0.06 | 6.16 | 0.90 ± 0.09** | 75.96 |
| | 95.50 | 0.97 ± 0.09** | 96.18 | 0.26 ± 0.06 | 7.33 | 0.65 ± 0.08** | 44.24 |
| | 47.45 | 0.80 ± 0.05** | 73.75 | 0.25 ± 0.04 | 6.97 | 0.55 ± 0.08** | 31.17 |
| | 23.88 | 0.62 ± 0.05** | 50.53 | 0.24 ± 0.04 | 5.22 | 0.48 ± 0.06** | 22.45 |
| | 11.94 | 0.36 ± 0.07** | 17.65 | 0.23 ± 0.05 | 4.83 | 0.39 ± 0.05** | 10.85 |
| | 5.97 | 0.33 ± 0.05** | 13.13 | 0.24 ± 0.03 | 4.97 | 0.33 ± 0.04 | 3.91 |

Note:
compared with the viral control group, **P < 0.01.

Experimental Example 2: Pharmacodynamic Evaluation of the Di-XYW Compound According to the Present Invention for Treating HSV-I Viral Keratitis in Mice 1. Objective The di-XYW compound of the present invention (the sample obtained in Example 5) was administered by eye drops, and the pharmacodynamic evaluation was carried out using the pathological change of HSV-I viral keratitis in mice as the disease model.

2. Methods 8-week-old C57 mice (25 mice, weighing 22 g-25 g) were used to establish HSV-I viral keratitis models in their right eyes. During the modeling process, sterile 25G needles were used to make #-shaped/*-shaped/parallel scratches on the cornea of all animals' right eyes. The depth of the scratches must be in the superficial layer, and could not penetrate the stroma. The depth of the scratches for each eye was moderately uniform, and the scratches were evenly distributed, and then a fiber syringe was used to drop 4 μl of HSV-I virus solution mixed well (titer: $2.0 \times 10^6$ PFU/ml), to finish modeling. After 1 day of modeling, the right eye of the animal was scored for HSV-I viral keratitis, and 20 mice with successful and uniform modeling were selected for inclusion in the experiment, which were randomly divided into two groups: a modeling group (Ctrl) and a di-XYW compound group, with 10 mice in one group. The surface of the right eye of the animal was treated with a corresponding solvent (Ctrl group, with physiological saline as the solvent) or a di-XYW compound at a concentration of 500 μg/ml (using physiological saline as the solvent), by administering every other day. On the day of administration, each eye should be administrated 5 times, 10 μl for each time, for 2 weeks. The pathological change of keratitis was scored before eye drops (Day 0) and on days 1, 3, 7, and 14 after eye drops (that was summarized as clinical scores, with scoring criteria shown in Table 7), followed by analysis and comparison.

TABLE 7

Scoring criteria for pathological change of viral keratitis (VK).

| Corneal ulcer | Score |
|---|---|
| Ulcer depth | |
| No ulcer | 0 |
| Mild corneal opacity, clear iris texture. | 1 |
| Grayish white opacities in the superficial layer of the cornea, and observing iris texture. | 2 |
| Grayish white opacities in the deep layer of the cornea, and unable to see clear iris texture. | 3 |
| Dense, grayish white opacities in the entire layer of the cornea, and unable to clearly see the anterior chamber. | 4 |
| Ulcer area | |
| No ulcer. | 0 |
| 0 < ulcer area ≤ 1/4 corneal area. | 1 |
| 1/4 < ulcer area ≤ 2/4 corneal area. | 2 |
| 2/4 < ulcer area ≤ 3/4 corneal area. | 3 |
| 3/4 < ulcer area ≤ 4/4 corneal area. | 4 |
| Ulcer morphology | |
| No ulcer. | 0 |
| Mild surface irregularity. | 1 |
| Rough and slightly swollen corneal surface. | 2 |
| Severe edema, swelling of descemet's membrane. | 3 |
| Corneal perforation or severe swelling of descemet's membrane. | 4 |
| Corneal neovascularization (=Vascular degree * Vascular area) | |
| Vascular degree | |
| No neovascularization in cornea. | 0 |
| New blood vessels that grow centripetally, but do not reach the center of the pupil or exceed the corneal radius. | 1 |
| New blood vessels reach the center of the pupil or exceed the corneal radius. | 2 |
| Vascular area | |
| No staining | 0 |
| 0 < dyeing area ≤ 1/4 corneal area. | 1 |
| 1/4 < dyeing area ≤ 2/4 corneal area. | 2 |
| 2/4 < dyeing area ≤ 3/4 corneal area. | 3 |
| 3/4 < dyeing area ≤ 4/4 corneal area. | 4 |

3. Results

Figure 18:
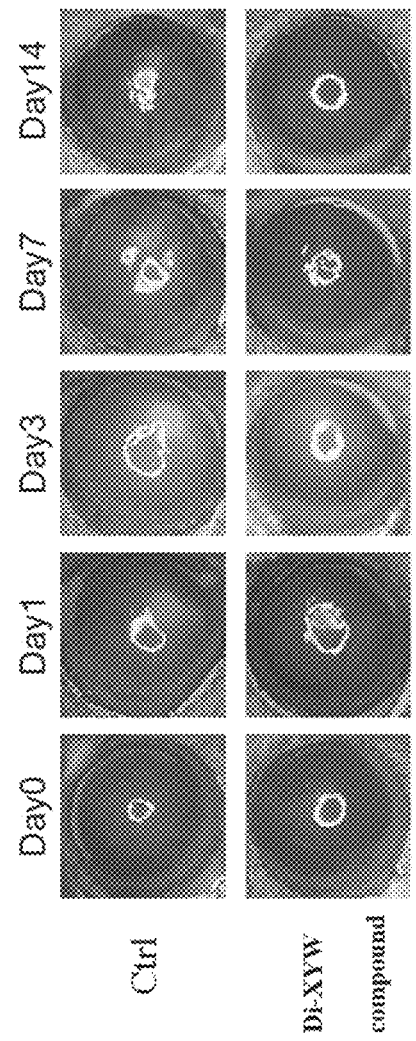
FIG. 18. The morphological changes of mouse cornea before eye drops of bi-XYW compound according to the present invention, as well as days 1, 3, 7, and 14 after its eye drops.
Figure 19:
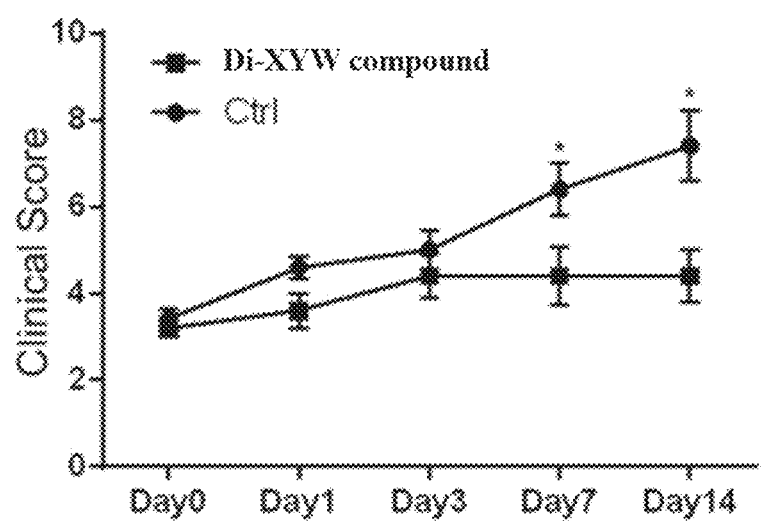
FIG. 19. The clinical score changes of mouse keratitis before eye drops of bi-XYW compound according to the present invention, as well as days 1, 3, 7, and 14 after its eye drops.

After 1 day of modeling, the right eye of each mouse showed typical corneal ulcer signs of HSV-I viral keratitis. 20 mice with uniform modeling were used in the experiment and randomly divided into groups. The experimental results indicated that the di-XYW compound had a good therapeutic effect on HSV-I viral keratitis, manifested as effectively reducing corneal edema, corneal ulcer depth and turbidity during the progression of disease, and improving the infiltration depth of keratitis. After 1 and 2 weeks of eye drop administration of di-XYW compound at 500 μg/ml, there were statistically significant differences in keratitis pathological changes (FIG. 18) and clinical score changes (FIG. 19) compared to the model control group (Ctrl) (*P<0.05).

4. Conclusion

The di-XYW compound of the present invention could effectively inhibit the pathological changes of HSV-I viral keratitis in mice.

In summary, the present invention provided a biflavone compound, which had excellent inhibitory activities against HSV-I, and showed significant effects on virus replication and direct inactivation in a dose-dependent manner; the compound of the present invention could effectively prevent and/or treat viral keratitis caused by HSV-I. Moreover, the compound of the present invention had good water solubility and low toxicity, and could be made into external preparations against HSV-I, such as eye drops, eye ointments, as well as ointments, creams, gels, films, paints and the same for external use, which had good safety and broad application prospects.

The invention claimed is:

1. A compound of Formula I, or a salt thereof, or a stereoisomer thereof,

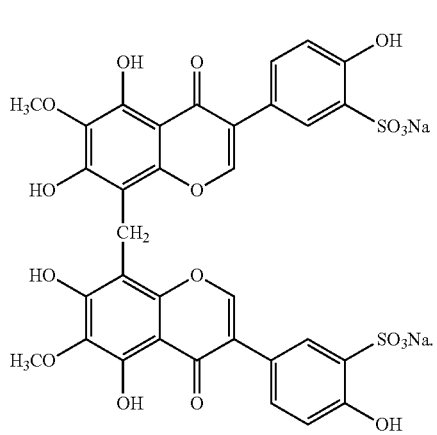

Formula I

2. A method for preparation of the compound of Formula I according to claim 1, comprising:

Step A: reacting compound 1 with formaldehyde in a solvent to obtain a reaction product; and Step B: purifying the reaction product to obtain the compound of Formula I, wherein, in Formula I, $R_1$ is —$OCH_3$, $R_2$ is —OH, $R_3$ is —$SO_3Na$, and $R_4$ is —OH,

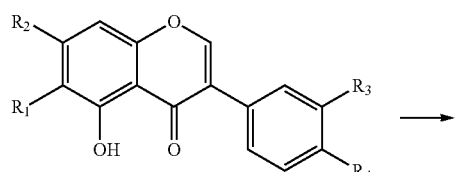

Compound 1

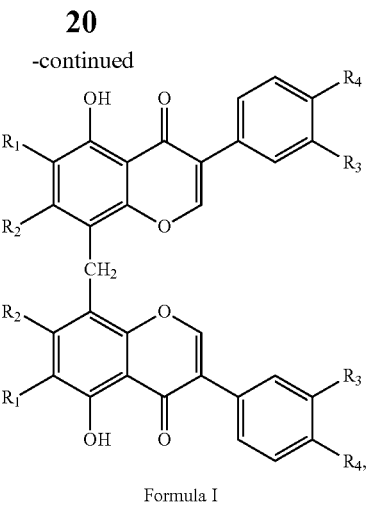

Formula I wherein, in Step A, the solvent is water or formaldehyde;

wherein, in Step (B), purifying is performed by preparative HPLC, silica gel column chromatography, thin-layer chromatography, silica gel dry column chromatography, or Sephadex gel column chromatography; and wherein the preparative HPLC is carried out in a preparation column comprising a packing material that is octadecylsilane chemically bonded silica gel at a column temperature of room temperature, using a mobile phase that is a mixed solvent of methanol and water.

3. A pharmaceutical preparation, comprising an active ingredient selected from the compound of Formula I according to claim 1, the salt thereof, the stereoisomer thereof, and a pharmaceutically acceptable excipient or adjuvant.

4. The pharmaceutical preparation according to claim 3, wherein the pharmaceutical preparation is an external preparation.

5. The pharmaceutical preparation according to claim 3, wherein the pharmaceutical preparation is selected from eye drops, eye ointments, creams, gels, films, and paints.

6. The method according to claim 2, wherein, in Step A, the weight/volume ratio of compound 1 to formaldehyde is 1:(5-10) g/ml.

7. The method according to claim 2, wherein, in Step A, the reaction is carried out by heating under reflux in a water bath for 8-10 hours.

8. The method according to claim 2, wherein, in Step A, further comprising recovering the solvent under reduced pressure, followed by drying, to obtain the crude product.

9. The method according to claim 2, wherein the purification is carried out by loading a sample in chloroform in a pre-packed silica gel column, and eluting using an eluent that is a mixed solution of chloroform and methanol at a volume ratio of 10:1 to 1:1, and the volume/weight ratio of eluent to the reaction product for each gradient is 500 ml:1 g.

10. The method according to claim 2, wherein purification is carried out by thin layer chromatography and silica gel dry column chromatography using an eluent that is a mixed solution of chloroform and methanol at a volume ratio of 100:30.

11. The method according to claim 2, wherein purification is carried out by Sephadex gel column chromatography in which a sample is wet loaded in a pre-packed column in 20% ethanol in water, and then eluted using a mixed solution of ethanol and water with a volume ratio of 10:2 to 10:10 and the volume/weight ratio of eluent to the reaction product is 500 ml:1 g.

* * * * *